Figure 1:
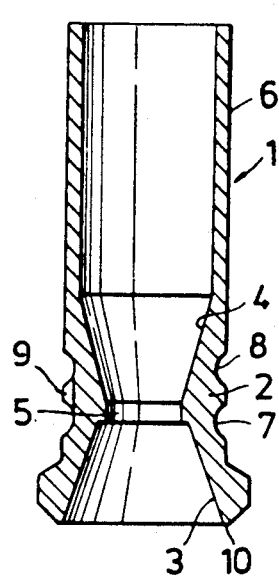

United States Patent [19]
Söderberg

[11] Patent Number: 5,078,606
[45] Date of Patent: Jan. 7, 1992

[54] METHOD FOR AFFIXING A DENTAL PROSTHESIS

[75] Inventor: Per O. Söderberg, Stockholm, Sweden

[73] Assignee: Astra Meditec Aktiebolag, Molndal, Sweden

[21] Appl. No.: 469,799

[22] Filed: Jan. 22, 1990

Related U.S. Application Data

[63] Continuation of Ser. No. 183,892, Apr. 20, 1988, abandoned.

[30] Foreign Application Priority Data

Apr. 22, 1987 [SE] Sweden ................................ 8701654

[51] Int. Cl.$^5$ .................................................. A61C 8/00
[52] U.S. Cl. ..................................... 433/173; 433/174
[58] Field of Search ............... 433/173, 174, 175, 176, 433/213, 214, 215

[56] References Cited

U.S. PATENT DOCUMENTS 3,708,883  1/1973  Flander ............................ 433/174
4,708,654  11/1987  Branemark ...................... 433/213
4,744,753  5/1988  Ross ................................. 433/214
4,746,293  5/1988  Lundgren et al. ................. 433/173

FOREIGN PATENT DOCUMENTS 2628485  1/1977  Fed. Rep. of Germany ...... 433/173
8504274  6/1987  Sweden .
8502337  6/1985  World Int. Prop. O. .......... 433/174

OTHER PUBLICATIONS

T. Jemt, Modified single and short-span restorations supported by osseointegrated fixtures in the partially edentulous jaw, The Journal of Prosthetic Dentistry, Feb. 1986.

Primary Examiner—John J. Wilson
Attorney, Agent, or Firm—White & Case

[57] ABSTRACT

A socket for use in preparing a dental prosthesis and in attaching the prosthesis to pillars attached to the patient's jawbone has a thin-walled tubular extension portion that is long enough to extend entirely through an impression material for the first mold used in preparing the prosthesis and/or through the bridge element of the prosthesis. One or more grooves on the socket enhance retention of the first mold and the bridge element.

3 Claims, 2 Drawing Sheets

U.S. Patent     Jan. 7, 1992     Sheet 2 of 2     5,078,606

METHOD FOR AFFIXING A DENTAL PROSTHESIS

This application is a continuation of application Ser. No. 183,892, filed on Apr. 20, 1988, now abandoned.

TECHNICAL FIELD

The present invention is related to a socket for carrying a dental prosthesis, in particular a dental prosthesis which is fixed to one or more implants attached into the jaw-bone of a patient. The object of the invention is to achieve a socket which may make part of a finished prosthesis and which additionally can be used as an aid during one or more steps in the work of preparing such a prosthesis. A further object is to reduce the number of parts making up a dental implant system.

STATE OF THE ART

From WO 85/02337 is known an implant for fixing of dental prostheses which has a conical socket-shaped part (7) against which the dental prosthesis may be fixed. Said socket-shaped part may however not, in the embodiment shown, be used as an aid in the work of preparing a prosthesis.

From Adell et al., Int. J. Oral Surg. 10 (1981), page 388 is known a dental implant system wherein the device for fixing of a prosthesis is a gold cylinder (k). Neither may this cylinder be used in the work of preparing a prosthesis. Instead there is used thereby separate impression copings (g and h), which in a first step are attached to spacing elements (c and d) attached to an implant, whereupon they are cast into a negative impression model, and then casting dummies for the spacing means are attached to said impression copings and cast into plaster. After removal of the impression copings the gold cylinders may be attached to the casting dummies, and a prosthesis is built thereon. This implant system has as a substantial disadvantage the fact that different details are required in the work of preparing the prosthesis and in the finished prosthesis, which in addition to the increased cost implies a practical drawback. A further component in the form of an extended screw may also be required in taking the negative impression model. Further, the impression copings have a fixed length and cannot be adjusted upon need of a varying length, e.g. conditioned by the space in the oral cavity.

DESCRIPTION OF THE INVENTION

According to the present invention the disadvantages with previously known constructions are avoided. Thus, there is provided a socket for carrying a dental prosthesis, which socket comprises a supporting part which at one end thereof is provided with a supporting surface for bearing against a supporting surface on a spacing element or pillar attached to the jaw-bone of a patient, and which further has means for securing of the socket against the spacing element. The socket is characterized in that the opposite end of the supporting part, beyond the means for securing the socket, is provided with a tubular thinwalled extension, which may form a channel through an impression material and/or a prosthetic material.

Preferably the bearing surfaces of the socket and the spacing element are complementary conical surfaces around which may be arranged planar control surfaces, however, also planar or differently shaped bearing surfaces may be used. The means for securing the socket against the spacing element may consist of a joint known per se, e.g. a screw joint. According to an embodiment of the invention this means comprises an inner conical supporting surface shaped for bearing against the conical head of a screw by which the socket is attached to the pillar. Alternatively, the supporting surface and the screw head may be planar. The spacing element may preferably consist of a single element, which in a manner known per se is attached to the jaw-bone via an osseointegrated root element anchored therein.

The tubular extension of the socket is thinwalled according to the invention. Thereby is achieved the possibility of grinding the socket down into level with the upper edge of the prosthesis or prosthetic part after building of a prosthesis or a part thereof, such as a dental bridge. In a corresponding manner the socket may be adjusted as to length on taking impressions or in process preparative work.

According to a preferred embodiment of the invention the supporting part of the socket has in the outer surface thereof one or more annular grooves for facilitating the casting or glueing of the socket into the posthetic part.

The socket according to the invention is made of metal such as stainless steel, preferably made of titanium or a titanium alloy. It has been found to be possible to cast a titanium socket according to the invention into a dental bridge of gold alloy.

Figure 2:
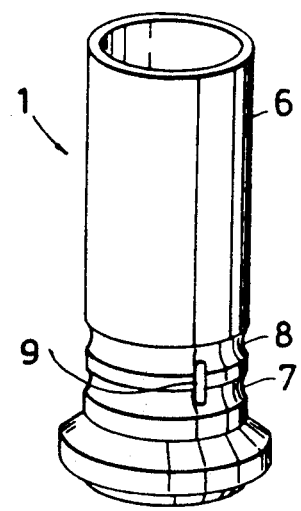
Figure 3:
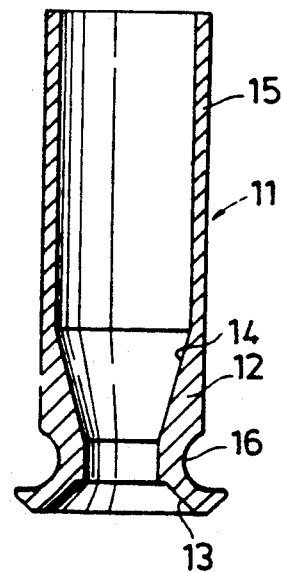
Figure 4:
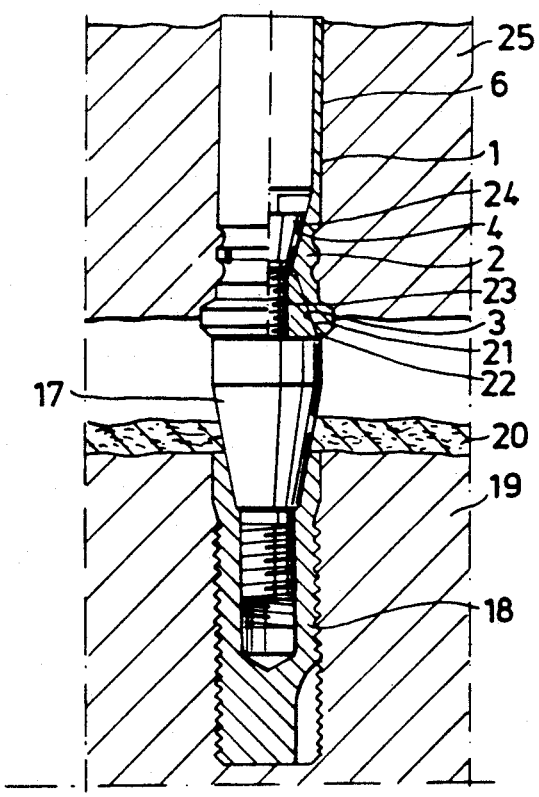
Figure 5:
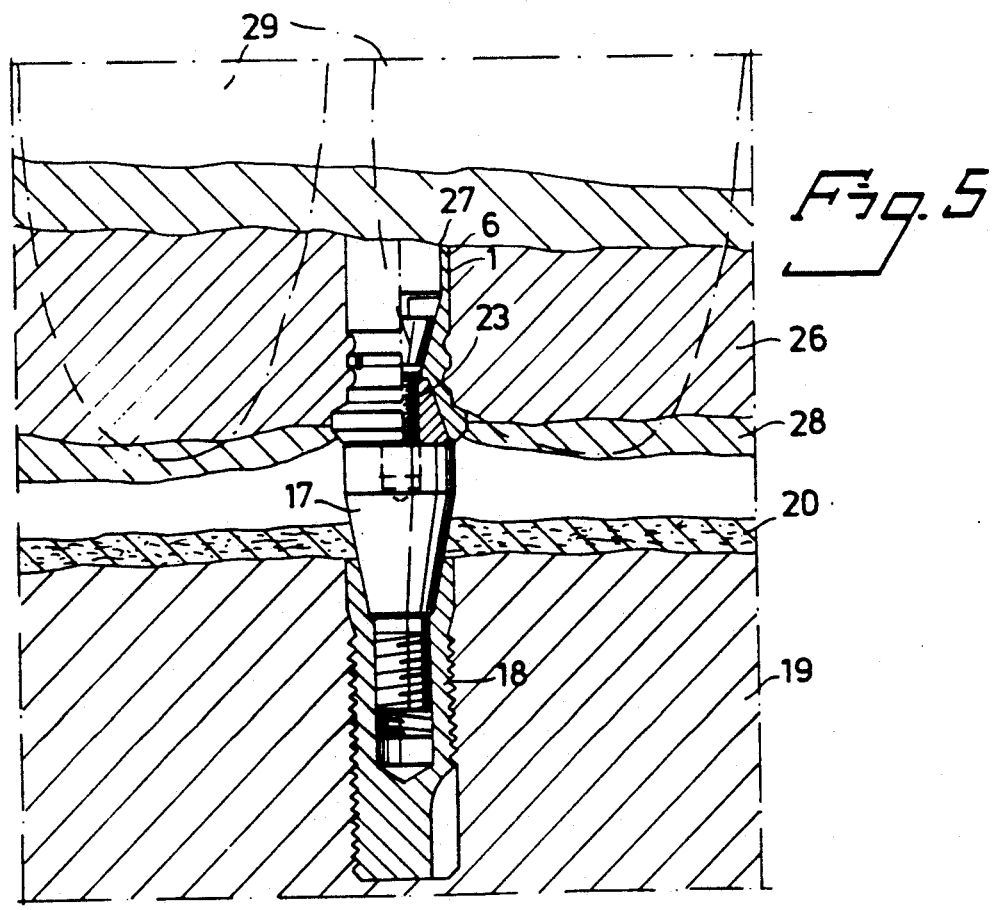

The invention is described further with reference to the appended drawings, where FIG. 1 shows a lengthwise cross section through a socket according to one embodiment of the invention, FIG. 2 shows the socket in a FIG. 1 in a view at an angle from above, FIG. 3 shows a lengthwise cross section through a socket according to another embodiment of the invention, FIG. 4 shows an implant combination comprising a socket according to the invention on building of an impression model, and FIG. 5 shows an implant combination comprising a socket according to the invention in a finished prosthesis.

In FIGS. 1, 2, 4 and 5 is denoted with 1 a socket according to the invention. The socket has a carrying part 2 which at its lower end has an inner conical supporting surface 3 broadening towards the end, for bearing against a complementary supporting surface on a spacing element. The supporting part of the socket further has an inner conical bearing surface 4 widening towards the upper end of the socket, for bearing against the conical head of a screw. The cavities defined by supporting the bearing surfaces 3 and 4 are in connection with each other via a short cylindrical bore 5. A tubular thinwalled extension 6 of the socket, made in one piece with the socket, is arranged at the upper end of the supporting part 2. The extension 6 has a length exceeding the length of the supporting part. As apparent from the drawing the wall thickness of the thinwalled extension 6 is substantially less than the wall thickness of the supporting part 2. Two annular grooves 7 and 8 are arranged around the supporting part. Between these grooves notches 9 are arranged for securing the socket against rotation in the impression and/or prosthetic material. The lower end of the socket has a planar control surface 10 adjacent to the conical supporting surface 3.

In FIG. 3 the socket is denoted 11, the bearing part 12, the lower conical supporting surface of the bearing part, which supporting surface has a larger cone angle than the supporting surface 3 in FIG. 1, is denoted 13 and is shaped for bearing against a spacing element with the corresponding conicity. The upper conical bearing surface of the supporting part, which surface is to bear against a screw, is denoted 14, and a tubular extension is denoted 15. The supporting part has an annular groove 16.

In FIGS. 4 and 5 17 denotes a pillar, which is a spacing element, which via an osseointegrated root screw is attached to the jaw-bone 19 of a patient. The tissue covering the jaw-bone is denoted 20. The pillar has an outer conical supporting surface 21. Between the lower end surface of the socket and a shoulder on the pillar there is a narrow gap 22. A screw for assembling the socket and the pillar is denoted 23 and has a conical head 24 which bears against the bearing surface 4. An impression or casting material used during the prosthesis preparing work is denoted 25 (FIG. 4), while a gold alloy dental bridge making part of a prosthesis, in which bridge the titanium socket is cast, is denoted 26 (FIG. 5). After casting of the socket into the bridge the extension 6 of the socket is ground down at 27 in level with the upper surface of the dental bridge 26. The dental bridge is baked into a prosthetic material 28 of acrylic resin, in which false teeth 29 are attached.

A manner of operation on using the socket according to the invention is in essence as follows. Bores for root screws 18 are drilled into the jaw-bone 19. The root screws are screwed in and are allowed to osseointegrate in a known manner. After uncovering of the upper ends of the root screws, pillars 17 are screwed in, which pillars usually are allowed to heal in under cover of a healing cap attached over the conical supporting surface 21 thereof. The healing cap is removed and sockets 1 are paced on the pillars and attached with screws 23. If desired, a plastic impression material may be placed over the socket for a bite recording to be used by the dental technician in the final prosthesis preparation. When needed the sockets are taken out and adjusted as to length in a first step by grinding down, whereupon they are remounted. The ends of the sockets are sealed with a plastic compound, whereupon an impression tray filled with plaster is depressed over the sockets, whereby the plaster is depressed as far as shown in FIG. 4 or preferably all the way down to the tissue 20, and the plaster is allowed to solidify. The seal over the ends of the sockets is removed, the screws 23 are released and the plaster impression is removed. Pillar dummies with conical supporting surfaces identical to the supporting surfaces 21 of the pillars are attached in the sockets by the screws 23 and are cast into plaster. The first plaster impression is removed and broken down to uncovering of the sockets 1; alternatively new similar sockets 1 are taken, and the sockets are mounted on the pillar dummies. A bridge construction is modelled of wax or plastic material and is released from the pillar dummies by removing the screws 23, whereupon the notches 9 of the socket prevent the rotation thereof in the plastic or wax frame-work. A mould is prepared by depressing the bridge structure into a mould compound and burning out of the wax or plastic material. A dental bridge 26 is cast of a metal alloy onto the sockets whereupon projecting parts of the sockets are ground down to the extent required and prosthesis building is done in a manner known per se.

I claim:

1. A method of preparing and affixing a dental prosthesis comprising the steps of:
   (a) providing a means for supporting a plurality of sockets in the jaw of a patient, the supporting means including a plurality of implants;
   (b) implanting said implants into the jawbone of a patient;
   (c) providing a plurality of sockets, each having a first end and a thin-walled tubular extension portion extending from the first end a distance sufficient to extend entirely through an impression material used in the preparation of a conventional prosthesis or entirely through a conventional bridge element of the prosthesis;
   (d) mounting the first end of sockets on the supporting means so as to be supported by the implants;
   (e) forming an impression about the sockets;
   (f) releasing the sockets from the supporting means and removing the impression from the mouth of the patient;
   (g) affixing a dummy support means to the sockets and forming a second impression about the dummy support means;
   (h) removing the first impression from the second impression;
   (i) forming a bridge material about a plurality of sockets while mounted on the dummy support means;
   (j) forming a dental bridge about the sockets using the bridge material; and
   (k) mounting the first end of sockets on the supporting means such that the sockets and dental bridge are supported by the implants.

2. A method according to claim 1, wherein the implants are root screws and the supporting means includes spacer elements which are mounted on the implants and which have a supporting surface for supporting the sockets, wherein the sockets include an internal hole opening at the supported surface and at a shoulder facing away from said one end, the hole and shoulder being adapted to receive a fastener by which the socket is fastened to the spacer element.

3. A method according to claim 2, wherein the dummy support means comprises dummy spacer elements, and wherein the dental bridge is formed by modelling a bridge structure on the sockets while mounted on the dummy spacer elements, removing the bridge structure and sockets from the dummy spacer elements, and thereafter preparing a mold from the bridge structure, casting a dental bridge onto the sockets, grinding down the projecting parts of the thin-walled extensions of the sockets, and forming a prosthesis on the bridge.

* * * * *